United States Patent
Capriotti et al.

(10) Patent No.: US 10,314,914 B2
(45) Date of Patent: *Jun. 11, 2019

(54) IODOPHOR COMPOSITION AND METHODS OF USE

(71) Applicant: Veloce BioPharma, LLC, Fort Lauderdale, FL (US)

(72) Inventors: Joseph Capriotti, Christiansted, VI (US); Kara Capriotti, Fort Washington, PA (US); Jesse Pelletier, Miami, FL (US); Kevin Stewart, Christiansted, VI (US)

(73) Assignee: Veloce BioPharma, LLC, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,222

(22) PCT Filed: Jan. 15, 2016

(86) PCT No.: PCT/US2016/013660
§ 371 (c)(1),
(2) Date: Jul. 17, 2017

(87) PCT Pub. No.: WO2016/118424
PCT Pub. Date: Jul. 28, 2016

(65) Prior Publication Data
US 2018/0008715 A1    Jan. 11, 2018

Related U.S. Application Data

(60) Provisional application No. 61/187,973, filed on Jul. 2, 2015, provisional application No. 62/105,613, filed on Jan. 20, 2015.

(51) Int. Cl.
| | | |
|---|---|---|
| *A61K 8/00* | (2006.01) | |
| *A61K 47/38* | (2006.01) | |
| *A61K 33/18* | (2006.01) | |
| *A61K 47/58* | (2017.01) | |
| *A61K 47/20* | (2006.01) | |
| *A61K 9/06* | (2006.01) | |
| *A61K 9/00* | (2006.01) | |
| *A61K 47/32* | (2006.01) | |

(52) U.S. Cl.
CPC ............ *A61K 47/38* (2013.01); *A61K 9/0014* (2013.01); *A61K 9/0048* (2013.01); *A61K 9/06* (2013.01); *A61K 33/18* (2013.01); *A61K 47/20* (2013.01); *A61K 47/32* (2013.01); *A61K 47/58* (2017.08)

(58) Field of Classification Search
None
See application file for complete search history.

(56) References Cited

U.S. PATENT DOCUMENTS

| | | |
|---|---|---|
| 3,551,554 A | 12/1970 | Herschler |
| 4,652,557 A | 3/1987 | Sandborn |
| 5,516,808 A | 5/1996 | Sawaya |
| 6,391,879 B1 | 5/2002 | Reeves |
| 7,462,362 B2 | 12/2008 | Kepka et al. |
| 8,512,724 B2 | 8/2013 | Tarrand |
| 9,770,466 B2 * | 9/2017 | Capriotti ............... A61K 31/79 |
| 2003/0049320 A1 | 3/2003 | Bhagwatwar et al. |
| 2006/0165747 A1 | 7/2006 | Rolf |
| 2009/0162301 A1 | 6/2009 | Tarrand |
| 2009/0263345 A1 | 10/2009 | Capriotti et al. |
| 2011/0217260 A1 | 9/2011 | Shantha et al. |
| 2012/0003174 A1 | 1/2012 | Capriotti et al. |
| 2013/0089510 A1 | 4/2013 | Capriotti et al. |

FOREIGN PATENT DOCUMENTS

| | | |
|---|---|---|
| GB | 2275191 A | 8/1994 |
| WO | WO 2009-151619 A1 | 12/2009 |
| WO | WO 2012/154740 A1 | 11/2012 |

OTHER PUBLICATIONS

Berkelman, Ruth, et al., Journal of Clinical Microbiology, Apr. 1982, p. 635-639 vol. 15, No. 4.
International Search Report in PCT/US2012/036942.
K. Capriotti, et al., A Novel Topical 2% Povidone-Iodine Solution for the Treatment of Common Warts: A Randomized, Double-blind, Vehicle-Controlled Trial, Dermatol Ther., Nov. 3, 2015 (DOI 10.1007/s13555-015-0086-1) (open access at Springerlink.com).
K. Capriotti, et al., Molluscum Contagiosum Viral Infention Treated With a Dilute Povidone-Iodine/Dimethylsulfoxide Prepartion, Derm Ther. Dec. 21, 2015 (DOI 10.1007/s13555-015-0091-4) (open access at Springerlink.com).
K. Capriotti and J. Capriotti, Chemotherapy-associated paronychia treated with a dilute povidone-iodine/dimethyl sulfoxide preparation, Clin. Cosmetic and Investigational Dermatology 2015:8 pp. 489-491.
International Search Report in PCT/US2014/025470.
International Search Report and IPRP/Written Opinion in PCT/US2012/065298.
International Preliminary Report on Patentability (IPRP) in PCT/US2016/013660.

\* cited by examiner

*Primary Examiner* — Susan T Tran
(74) *Attorney, Agent, or Firm* — Studebaker & Brackett PC

(57) ABSTRACT

Described are stable topical formulations useful in the treatment of viral wart infection, demodex infection and bacterial infection of the skin, and genitalia and the method of treating viral wart infection, demodex infection and bacterial infection of the skin, and genitalia with said compositions.

13 Claims, No Drawings

IODOPHOR COMPOSITION AND METHODS OF USE

BACKGROUND OF THE INVENTION

Millions of human patients suffer from viral infection or viral wart infection, demodex infection, fungal or yeast infection, or bacterial infection of the skin, hair follicle, or genitalia. Viral or wart infection, demodex infection, fungal or yeast infection, or bacterial infection of the eyelids, conjunctiva, cornea, ocular surface or Meibomian glands, can manifest as blepharitis—an inflammatory condition of the eyelid.

Verruca vulgaris, the medical term for wart, can arise anywhere on the body and serves as an umbrella term for all warts. Warts can result from viral infections that are most often associated with Human Papilloma Virus (HPV) or Molluscum Contagiosum Virus (MCV).

Human papilloma viruses (HPV) are a large group of approximately 100 genotypes of DNA tumor viruses that infect the epithelia of skin or mucosa and cause warts. Verruca vulgares (common warts) present clinically as hyperkeratotic, exophytic and dome-shaped papules or nodules associated with HPV-1, 2 or 4. They are most commonly found on fingers, dorsal hands, and other sites prone to trauma such as knees or elbows, but they may occur in any anatomic location.

Genital infection with HPV can result from intimate contact with individuals harboring clinical or subclinical HPV infection, and is one of the most common sexually transmitted diseases among adolescents and adults. Prevalence of HPV infection in the adult population differs depending upon geographical location, but typically ranges from 20% to 45% of all populations. In the US, 20 million people have genital HPV infection at any given time, amounting to an annual cost burden of $6 billion per year in healthcare dollars spent for sexually transmitted infections (second only to HIV).

Non-genital viral infections of the skin may occur via direct person-to-person skin contact, or indirectly through contaminated surfaces in a publicly accessed area, such as a public swimming pool or gymnasium. The skin is exposed to the virus through minor abrasions and infection is promoted via maceration of the epithelia. Autoinoculation is common as well. Non-genital varieties of skin warts occur in 20% of schoolchildren with equal frequency in both sexes.

Verruca palmares et plantares (palm and sole warts) are thick, endophytic papules and plaques with numerous thrombosed capillaries that often coalesce into large dome-like elevations. They are often painful due to deep inward growth and are notoriously difficult to eradicate. HPV-1, 2, 27 and 57 are the most common culprits of palm or sole warts.

Verrucae plana (flat warts) are skin-colored or pink, smooth-surfaced, slightly elevated and flat-topped papules most commonly located on the dorsal hands, legs, or face. They are often in a linear array as scratching or shaving can spread them. HPV types 3 and 10 cause this phenotype.

Condyloma acuminata (genital warts) are found on the external genitalia and perineum, perianal, or in adjacent areas such as the inguinal folds or mons pubis. They can range in size from a few millimeters to centimeters and are most commonly sessile, smooth-surfaced exophytic papillomas that can be skin colored, brown or white. They lack the thick hyperkeratotic layer of common warts found on skin. HPV-6 and 11 cause genital warts in the majority of cases.

Infection of the skin surrounding or forming part of the eye can also occur. Blepharitis is a commonly encountered condition affecting approximately 15% of the population, and represents an inflammatory condition of the eyelids. Blepharitis may involve the dermis, eyelashes, tarsal conjunctiva, mucocutaneous junction or meibomian glands and is most often caused by gram positive bacterial infection, such as *Stapylococcus, Corynebacterium*, and *Pripionibacterium* species. However, other agents causing blepharitis include viral, demodex (mite), or yeast infections, seborrhea, rosacea, and hormonal dysregulation.

Left untreated, blepharitis may cause dry eye exacerbation, loss of cilia, corneal ulceration, and impart increased risk of endophthalmitis after cataract surgery. For facility in understanding, it is commonly compartmentalized into inflammation affecting the structures of the anterior, posterior lid margin or both.

Anterior blepharitis most commonly presents as anterior lid and lash crusting with or without the presence of collarettes. Other manifesations may also include skin or lash flaking associated with seborrhea or angular inflammation particular to *Moraxella* or virus.

Posterior blepharitis is also commonly referred to as meibomian gland disease. Meibomian glands are responsible for the release of lipids into the tear film, effectively mitigating evaporative tear loss. Besides the chronic irritation, inflammation and erythema common to all blepharitis, the posterior variant may further be characterized by inspissation of the meibomian glands, keratinization of orifices, telangiectasia, and posterior margin lid thickening. Bacterial lipases stemming from the ocular flora may also act upon meibomian secretions creating free fatty acids which further disturb the ocular surface.

Current treatments for bacterial, demodex, fungal/yeast, and viral infections, including warts and ophthalmic conditions such as blepharitis, can be ineffective in that they treat only a subset of the causative agent of the infection. Many of the current treatments incorporate undesirable ingredients, such as steroids or other potentially harmful components.

A recent discovery by Capriotti, et al., has disclosed compositions comprising an iodophor, such as povidone-iodine (PVP-I) as an active ingredient, and dimethyl sulfoxide (DMSO) used as a penetration enhancer for the active ingredient. These compositions were shown to be useful for treating fungal infections of the skin and nails. See, e.g., US Publication No. US2014/0205559 (Capriotti '559), which is incorporated herein by reference in its entirety. PVP-I is a well-known antiseptic with a broad spectrum of activity against viral, fungal, and bacterial species, as well as demodex, and has no known bacterial, fungal or viral resistance. PVP-I has also been shown to inhibit the formation of biofilms and to eliminate biofilms that have already formed.

A variety of organic solvents, including dimethyl sulfoxide (DMSO), are known to enhance the percutaneous absorption of certain medicaments. The superiority of DMSO to other solvents for enhancing penetration and dermal retention was demonstrated in a study of the passage of 14C-labelled griseofulvin, dissolved in DMSO, dimethylacetamide, dimethylformamide, alcohol or benzene, through human skin in vitro. The ratio of penetration of griseofulvin in the various solvents was 60, 40, 7, 3, and 1, respectively. Even when a 50% solution of DMSO in water was used, the rate of penetration of 14C-hydrocortisone was markedly enhanced. Nevertheless, it has been a long-accepted in the pharmaceutical arts that DMSO enhances penetration for small molecules or low molecular weight (LMW) compounds or drugs, but does not enhance penetration of high molecular weight (HMW) compounds greater than about 10,000 Daltons, such as polymers.

It has been surprisingly discovered that DMSO is effective at enhancing penetration into the thick stratum corneum of the palms and soles. Moreover, DMSO has been only recently, and unexpectedly, been demonstrated to enhance penetration of povidone-iodine (PVP-I). PVP-I preparations range in molecular weights from 1,000 to 1,000,000 or more. Topical pharmaceutical compositions have been approved using only PVP grades K29-32. One acceptable PVP grade is PVP K30, which has a MW of 30,000 to 60,000 daltons (average MW of about 40,000 daltons). Accordingly, prior to the teachings of Capriotti '559, one skilled in the art would not employ DMSO in a topical pharmaceutical composition to enhance skin penetration of large molecules, polymers or high-molecular weight substances such as PVP-I.

Even in view of the teachings of Capriotti '559, however, it was unknown that particular topical gel formulations comprising an iodophor, such as PVP-I, in DMSO were particularly useful in treating certain viral, demodex, fungal/yeast, or bacterial infections manifesting as skin infections (e.g., warts) or ophthalmic conditions (e.g., blepharitis). Thus, the current invention is a significant advance to the art, and discloses the surprising and unexpected discovery that a topical gel composition comprising an iodophor such as PVP-I, DMSO, and a gelling agent can provide advantageous and unexpected results in the treatment of warts or other skin infections, including skin infection of the eye such as blepharitis.

SUMMARY OF THE INVENTION

The present invention concerns a topical gel composition comprising an iodophor, a penetration enhancer, and a gelling agent, wherein the composition is particularly effective in treating viral, demodex, fungal/yeast, or bacterial infection that can cause warts or blepharitis. Thus, the subject invention further comprises a method of treating viral, demodex, fungal/yeast, or bacterial infection using a topical gel composition as disclosed herein. The composition can further comprise optional pharmaceutically acceptable excipients or solvents or co-solvents.

A composition of the subject invention preferably comprises active pharmaceutical ingredient (API) recognized as appropriate and acceptable for use in a pharmaceutical preparation by the United States Food and Drug Administration (FDA). A preferred composition of the invention further comprises inactive ingredients or excipients recognized as appropriate and acceptable for use in a pharmaceutical preparation for topical administration. An FDA-approved API or acceptable inactive ingredient or excipient is referred to herein as "pharmaceutically acceptable." Accordingly, a topical composition, formulation, or preparation of the subject invention comprising a pharmaceutically acceptable API, inactive ingredient or excipient is referred to herein as a "pharmaceutically acceptable" topical composition.

Similarly, an ophthalmic composition of the subject invention comprising FDA-approved active or inactive ingredients acceptable for use in an ophthalmic preparation, is referred to herein as a "pharmaceutically acceptable ophthalmic composition," or "ophthalmically acceptable" composition, comprising API, excipient, or solvent which is "pharmaceutically acceptable" for ophthalmic use, or is "ophthalmically acceptable."

More particularly, the subject invention relates, in a preferred embodiment, to a stable topical composition comprising an iodophor having a molecular weight of greater than 10,000 Daltons, dimethyl sulfoxide (DMSO), and a gelling agent, and optional additional pharmaceutically or ophthalmically acceptable excipients or solvents or co-solvents.

A composition of the subject invention can be useful in a method for treating viral infection or viral wart infection, demodex infection, fungal or yeast infection, or bacterial infection of the skin, hair follicle, or genitalia, and can further be useful for treating blepharitis, which can be caused by viral wart infection, demodex infection, fungal or yeast infection, or bacterial infection of the eyelids, conjunctiva, cornea, ocular surface or Meibomian glands.

A topical gel composition of the subject invention is unexpectedly highly stable at room temperature in the presence of aqueous or anhydrous ingredients.

A topical gel composition of the subject invention comprises about 0.1% to about 10% povidone-iodine (PVP-I); about 30% to about 99% dimethyl sulfoxide (DMSO); and about 1% to about 10% gelling agent. The topical gel composition of the invention unexpectedly exhibits greater efficacy in treating skin infection or blepharitis, compared to a liquid composition substantially free of a gelling agent and comprising about 0.1% to about 10% povidone-iodine and about 30% to about 99% DMSO.

A preferred composition comprises about 1% to about 5% PVP-I. A more preferred composition can comprise about 1% PVP-I or about 2% PVP-I. A PVP-I employing povidone grade of K30 is preferred for use in the subject composition.

A preferred composition comprises about 30% to about 70% DMSO. A more preferred composition can comprise about 40% to about 49% DMSO, and even more preferably, about 44% DMSO.

A preferred composition comprises about 2% to about 5% gelling agent. A more preferred composition can comprise about 4% gelling agent. A particularly useful composition which has been prepared for testing comprises 2% PVP-I; 44% DMSO; 4% hydroxyethylcellulose, and 50% aqueous solvent. A preferred aqueous solvent is water or isotonic buffer.

A composition of the invention can include a gelling agent, as is well known in the art, which can be selected from a gum, agar, carrageenan, petrolatum, or a cellulosic polymer or the like. One preferred cellulosic polymer as a gelling agent is hydroxyethyl cellulose. An alternative cellulosic polymer gelling agent is hydroxymethyl cellulose.

A composition of the invention preferably comprises povidone-iodine, or PVP-I having an average molecular weight greater than 10,000. More preferably, the composition of the invention comprises PVP-I having an average molecular weight between about 20,000 to about 1,000,000. One preferred embodiment comprises PVP-I having an average molecular weight between about 30,000 to about 60,000, or greater. Each of the PVP-I ingredients is referred to herein as a "high molecular weight PVP-I," or "HMW PVP-I."

Another embodiment of a composition according to the subject invention is a stable, topical ophthalmic gel formulation comprising about 0.1% to about 10% povidone-iodine (PVP-I); about 30% to about 99% dimethyl sulfoxide (DMSO); and about 1% to about 10% gelling agent; wherein, each ingredient in the composition is ophthalmically acceptable, and the ophthalmic gel composition exhibits greater efficacy in treating infectious conditions of the eye or eyelid, compared to a liquid composition substantially free of a gelling agent and comprising about 0.1% to about 10% povidone-iodine and about 30% to about 99% DMSO.

A preferred ophthalmic gel composition comprises about 0.5% to about 5% PVP-I. A more preferred ophthalmic gel composition comprises about 1% to about 3% PVP-I, and a most preferred ophthalmic gel composition comprises about 1% PVP-I.

A composition of the invention preferably comprises povidone-iodine, or PVP-I having an average molecular weight greater than 10,000. More preferably, the composition of the invention comprises PVP-I having an average molecular weight between about 20,000 to about 1,000,000. One preferred embodiment comprises high molecular weight (HMW) PVP-I.

A preferred ophthalmic gel composition comprises about 30%/o to about 70% DMSO. A more preferred ophthalmic gel composition can comprise about 40% to about 49% DMSO, and even more preferably, about 44% DMSO.

A preferred ophthalmic gel composition comprises about 2% to about 5% gelling agent. A more preferred ophthalmic gel composition can comprise about 4% gelling agent. A particularly useful composition which has been prepared for use in treating infection of the eye or eyelid comprises 1% PVP-I; 44% DMSO; 4% hydroxyethylcellulose; and 51% aqueous solvent. A preferred aqueous solvent is water or isotonic buffer.

An ophthalmic gel composition of the invention can include a gelling agent, as is well known in the art, selected from a gum, agar, carrageenan, petrolatum, or a cellulosic polymer or the like. One preferred cellulosic polymer useful as a gelling agent is hydroxyethyl cellulose (HEC). An alternative cellulosic polymer gelling agent is hydroxymethyl cellulose.

The subject invention further concerns a method for treating, or inhibiting the growth of, warts, including genital warts, caused by human papilloma virus (HPV) or molluscum contagiosum virus (MCV). The method comprises, generally, one or more as needed administrations or topical applications of a topical gel of the invention, namely, a topical composition comprising an iodophor, DMSO, and a gelling agent, to the site, until the wart is eliminated, or its growth is substantially inhibited. In a preferred method, the subject gel composition is administered directly onto the wart as needed (PRN), preferably at least once per day (QD), or more preferably at least two times per day (BID) until results are seen, typically for about one week, up to about 24 weeks.

More particularly, a method of the subject invention comprises treating an infection of the skin, including skin of genitalia, by providing a composition as described herein, and applying an effective amount of a topical gel composition to a site of the infection as needed to reduce or eliminate the infection caused by or associated with one or more infectious agents selected from the group consisting of bacteria, demodex, fungus or yeast, and virus.

A preferred method of treating viral infection of the skin or genitalia comprises administration or application to a skin infection caused by or associated with human papilloma virus (HPV) or molluscum contagiosum virus (MCV). Preferably, the subject method can be used to reduce or eliminate a viral wart. The method can be carried out by application or administration of the composition to a skin infection on the skin of the face or genitalia.

Yet another aspect of the invention comprises a method of treating an infectious condition of the eye or eyelid, comprising applying an effective amount of a stable, topical ophthalmic gel composition to a site of the infection to reduce or eliminate the infection.

The method of the invention can be useful in treating blepharitis, conjunctivitis, corneal ulcer, HSV keratitis, conjunctival neoplasia, AC inflammation, post-operative endophthalmitis, and endophthalmitis after intravitreal or intracameral injection, which is caused by or associated with one or more infectious agents such as bacteria, demodex, fungus or yeast, or virus.

DETAILED DESCRIPTION OF THE INVENTION

The present invention concerns a topical gel composition comprising an antiseptic agent, a penetration enhancer, and a gelling agent. Preferably, the composition comprises povidone-iodine as the antiseptic agent, dimethylsulfoxide (DMSO) as the penetration enhancer, and a cellulosic gelling agent, such as hydroxyethylcelluose (HEC). The composition can, optionally, further comprise a lubricant or co-solvent, or other acceptable excipients. For example, a composition for treating an ophthalmic condition, such as blepharitis can include an ophthalmically acceptable excipient.

The subject composition is surprisingly useful for the treatment of viral wart infection of the skin, as well as viral, demodex, fungal/yeast or bacterial infection of the eyelids, conjunctiva, cornea, ocular surface and Meibomian glands, which can cause blepharitis.

A specific but non-limiting example of a formulation of the invention providing a useful pharmaceutical preparation comprises solid PVP-I dissolved or suspended in DMSO with one or additional co-solvents in solution and prepared as a gel or semi-solid.

In another embodiment, DMSO can be added to aqueous solutions of PVP-I. In an example DMSO can be present as a co-solvent with water in the range of 10%-99%. One embodiment of such a formulation could include a range of excipients such as sodium chloride, sodium dihydrogen phosphate monohydrate, disodium hydrogen phosphate anhydrous and water, as well as others known to those skilled in the art.

Percentages set forth herein are (w/w), with respect to the specified component in the overall composition, unless otherwise indicated. For example, a composition comprising 1% PVP-I and 45% DMSO has 1% PVP-I by weight, with respect to the total composition. For example, in an embodiment, a composition comprises povidone-iodine in the range of about 0.01% to about 15%. In another embodiment, a composition comprises povidone-iodine in the range between 0.05% and 12.5%. In another embodiment, a composition comprises povidone-iodine in the range between 0.05% and 10.0%. In another embodiment, a composition comprises povidone-iodine in the range between 0.1% and 10.0%. In another embodiment, a composition comprises povidone-iodine in the range between 0.1% and 5.0%. In another embodiment, a composition comprises povidone-iodine in the range between 0.25% and 9.0%. In another embodiment, a composition comprises povidone-iodine in the range between 0.2% and 2.5%. In another embodiment, a composition comprises povidone-iodine in the range between 0.5% and 7.5%. %. In another embodiment, a composition comprises povidone-iodine in the range between 0.5% and 1.0%. In another embodiment, a composition comprises povidone-iodine in the range between 0.75% and 5.0%, and in yet another embodiment, between 1.0% and 4.0%. In an embodiment, a composition comprises povidone-iodine in the range of about 0.1% to about 2.5%, about 0.2% to about 2.0%, about 0.3% to about 1.0%, and about 0.4% to about 0.75%.

In an embodiment, a composition comprises povidone-iodine of about 0.01%, about 0.05%, about 0.10%, about 0.15%, about 0.20%, about 0.25%, about 0.30%, about 0.35%, about 0.4/0%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.05%, about 1.10%, about 1.15%, about 1.20%, about 1.25%, about 1.30%, about 1.35%, about 1.40%, about 1.45%, about 1.50%, about 1.55%, about 1.60%, about 1.65%, about 1.70%, about 1.75%, about 1.80%, about 1.85%, about 1.90%, about 1.95%, about 2.00%, about 2.05%, about 2.10%, about 2.15%, about 2.20%, about 2.25%, about 2.30%, about 2.35%, about 2.40%, about 2.45%, about 2.50%, about 2.55%, about 2.60%, about 2.65%, about 2.70%, about 2.75%, about 2.80%, about 2.85%, about 2.90%, about 2.95%, about 3.00%, about 3.05%, about 3.10%, about 3.15%, about 3.20%, about 3.25%, about 3.30%, about 3.35%, about 3.40%, about 3.45%, about 3.50%, about 3.55%, about 3.60%, about 3.65%, about 3.70%, about 3.75%, about 3.80%, about 3.85%, about 3.90%, about 3.95%, about 4.00%, about 4.05%, about 4.10%, about 4.15%, about 4.20%, about 4.25%, about 4.30%, about 4.35%, about 4.4/0, about 4.45%, about 4.50%, about 4.55%, about 4.60%, about 4.65%, about 4.70%, about 4.75%, about 4.80%, about 4.85%, about 4.90%, about 4.95/0, about 5.00%, about 5.05%, about 5.10%, about 5.15%, about 5.20%, about 5.25%, about 5.30%, about 5.35%, about 5.40%, about 5.45%, about 5.50%, about 5.55%, about 5.60%, about 5.65%, about 5.70%, about 5.75%, about 5.80%, about 5.85%, about 5.90%, about 5.95%, about 6.00%, about 7.05%, about 7.10%, about 7.15%, about 7.20%, about 7.25%, about 7.30%, about 7.35%, about 7.40%, about 7.45%, about 7.50%, about 7.55%, about 7.60%, about 7.65%, about 7.70%, about 7.75%, about 7.80%, about 7.85%, about 7.90%, about 7.95%, about 8.00%, about 8.05%, about 8.10%, about 8.15%, about 8.20%, about 8.25%, about 8.30%, about 8.35%, about 8.406, about 8.45%, about 8.50%, about 8.55%, about 8.60%, about 8.65%, about 8.70%, about 8.75%, about 8.80%, about 8.85%, about 8.90%, about 8.95%, about 9.00%, about 9.05%, about 9.10%, about 9.15%, about 9.20%, about 9.25%, about 9.30%, about 9.35%, about 9.40%, about 9.45%, about 9.50%, about 9.55%, about 9.60%, about 9.65%, about 9.70%, about 9.75%, about 9.80%, about 9.85%, about 9.90%, about 9.95%, about 10.00%, about 10.05%, about 10.10%, about 10.15%, about 10.20%, about 10.25%, about 10.30%, about 10.35%, about 10.40%, about 10.45%, about 10.50%, about 10.55%, about 10.60%, about 10.65%, about 10.70%, about 10.75%, about 10.80%, about 10.85%, about 10.90%, about 10.95%, about 11.00%, about 11.05%, about 11.10%, about 11.15%, about 11.20%, about 11.25%, about 11.30%, about 11.35%, about 11.40%, about 11.45%, about 11.50%, about 11.55%, about 11.60%, about 11.65%, about 11.70%, about 11.75%, about 11.80%, about 11.85%, about 11.90%, about 11.95%, about 12.00%, about 12.05%, about 12.10%, about 12.15%, about 12.20%, about 12.25%, about 12.30%, about 12.35%, about 12.40%, about 12.45%, about 12.50%, about 12.55%, about 12.60%, about 12.65;%, about 12.70%, about 12.75%, about 12.80%, about 12.85%, about 12.90%, about 12.95%, about 13.00%, about 13.05%, about 13.10%, about 13.15%, about 13.20%, about 13.25%, about 13.30%, about 13.35%, about 13.40%, about 13.45%, about 13.50%, about 13.55%, about 13.60%, about 13.65%, about 13.70%, about 13.75%, about 13.80%, about 13.85%, about 13.90%, about 13.95%, about 14.00%, about 14.05%, about 14.10%, about 14.15%, about 14.20%, about 14.25%, about 14.30%, about 14.35%, about 14.40%, about 14.45%, about 14.50%, about 14.55%, about 14.60%, about 14.65%, about 14.70%, about 14.75%, about 14.80%, about 14.85%, about 14.90%, about 14.95%, about 15.00%, or any range determinable from the preceding percentages (for example, about 0.01% to about 0.05% or about 10.55% to about 12.50%).

In an embodiment, a composition comprises PVP-I in the range of about 0.01% to about 15%. In another embodiment, a composition comprises PVP-1 in the range between 0.05% and 12.5%. In another embodiment, a composition comprises PVP-I in the range between 0.05% and 10.0%. In another embodiment, a composition comprises PVP-I in the range between 0.1% and 10.0%. In another embodiment, a composition comprises PVP-I in the range between 0.1% and 5.0%. In another embodiment, a composition comprises PVP-I in the range between 0.25% and 9.0%. In another embodiment, a composition comprises PVP-I in the range between 0.2% and 2.5%. In another embodiment, a composition comprises PVP-I in the range between 0.5% and 7.5%. %. In another embodiment, a composition comprises PVP-I in the range between 0.5% and 1.0%. In another embodiment, a composition comprises PVP-I in the range between 0.75% and 5.0%, and in yet another embodiment, between 1.0% and 4.0%. In an embodiment, a composition comprises PVP-I in the range of about 0.1% to about 2.5%, about 0.2% to about 2.0%, about 0.3% to about 1.0%, and about 0.4% to about 0.75%.

In an embodiment, a composition comprises PVP-I at about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.25%, about 1.50%, about 1.75%, about 2.0%, about 2.25, about 2.5%, about 3.0%, about 3.5%, about 4%, about 4.5%, about 5%, about 7.5%, about 10%, about 12.5, or about 15.0%. In an embodiment, a composition comprises PVP-I at about 0.001%, about 0.002%, about 0.003%, about 0.004%, about 0.005%, about 0.006%, about 0.007%, about 0.008%, about 0.009%, about 0.01%, about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.05%, about 1.10%, about 1.15%, about 1.20%, about 1.25%, about 1.30%, about 1.35%, about 1.40%, about 1.45%, about 1.50%, about 1.55%, about 1.60%, about 1.65%, about 1.70%, about 1.75%, about 1.80%, about 1.85%, about 1.90%, about 1.95%, about 2.006, about 2.05%, about 2.10%, about 2.15%, about 2.20%, about 2.25%, about 2.30%, about 2.35%, about 2.40%, about 2.45%, about 2.50%, about 2.55%, about 2.60%, about 2.65%, about 2.70%, about 2.75%, about 2.80%, about 2.85%, about 2.90%, about 2.95%, about 3.00%, about 3.05%, about 3.10%, about 3.15%, about 3.20%, about 3.25%, about 3.39%, about 3.35%, about 3.40%, about 3.45%, about 3.50%, about 3.55%, about 3.6/0, about 3.65%, about 3.70%, about 3.75%, about 3.80%, about 3.85%, about 3.90%, about 3.95%, about 4.00%, about 4.05%, about 4.10%, about 4.15%, about 4.20%, about 4.25%, about 4.30%, about 4.35%, about 4.40%, about 4.45%, about 4.50%, about 4.55%, about 4.60%, about 4.65%, about 4.70%, about 4.75%, about 4.80%, about 4.85%, about 4.90%, about 4.95%, about 5.00%, about 5.05%, about 5.10%, about 5.15%, about 5.20%, about 5.25%, about 5.30%, about 5.35%, about 5.40%, about 5.45%, about 5.50%, about 5.55%, about 5.60%, about 5.65%, about 5.70%, about 5.75%, about 5.80%, about 5.85%, about 5.90%, about 5.95%, about 6.00%, about 7.05%, about 7.10%, about 7.15%, about 7.20%, about 7.25%, about 7.30%, about 7.35%, about 7.40%, about 7.45%, about 7.50%, about 7.55%, about 7.60%, about 7.65%, about 7.70%, about 7.75%, about 7.80%, about 7.85%, about 7.90%, about 7.95%, about 8.00%, about 8.05%, about 8.10%, about 8.15%, about 8.20%, about 8.25%[9], about 8.30%, about 8.35%, about 8.40%, about 8.45%, about 8.50%, about 8.55%, about 8.60%, about 8.65%, about 8.70%, about 8.75%, about 8.80%, about 8.85%, about 8.90%, about 8.95%, about 9.00%, about 9.05%, about 9.10%, about 9.15%, about 9.20%, about 9.25%, about 9.30%, about 9.35%, about 9.40%, about 9.45%, about 9.50%, about 9.55%, about 9.60%, about 9.65%, about 9.70%, about 9.75%, about 9.80%, about 9.85%, about 9.90%, about 9.95%, about 10.00%, about 10.05%, about 10.10%, about 10.15%, about 10.20%, about 10.25%, about 10.30%, about 10.35%, about 10.40%, about 10.45%, about 10.50%, about 10.55%, about 10.60%, about 10.65%, about 10.70%, about 10.75%, about 10.80%, about 10.85%, about 10.90%, about 10.95%, about 11.00%, about 11.05%, about 11.10%, about 11.15%, about 11.20%, about 11.25%, about 11.30%, about 11.35%, about 11.40%, about 11.45%, about 11.50%, about 11.55%, about 11.600%, about 11.65%, about 11.70%, about 11.75%, about 11.80%, about 11.85%, about 11.90%, about 11.95/0%, about 12.006, about 12.05%, about 12.10%, about 12.15%, about 12.20%, about 12.25%, about 12.306, about 12.35%, about 12.40%, about 12.45%, about 12.50%, about 12.55%, about 12.60%, about 12.65%, about 12.70%, about 12.75%, about 12.80%, about 12.85%, about 12.90%, about 12.95%, about 13.00%, about 13.05%, about 13.10%, about 13.15%, about 13.20%, about 13.25%, about 13.30%, about 13.35%, about 13.40%, about 13.45%, about 13.50%, about 13.55%, about 13.60%, about 13.65%, about 13.70%, about 13.75%, about 13.80%, about 13.85%, about 13.90%, about 13.95%, about 14.00%, about 14.05%, about 14.10%, about 14.15%, about 14.20%, about 14.25%, about 14.30%, about 14.35%, about 14.40%, about 14.45%, about 14.50%, about 14.55%, about 14.60%, about 14.65%, about 14.70%, about 14.75%, about 14.80%, about 14.85%, about 14.90%, about 14.95%, about 15.00%, or any range determinable from the preceding amounts (for example, about 0.001% to about 1.75% or about 0.05% to about 15.0%).

In another embodiment, a composition comprises PVP-I at about 1%, about 2%, about 3%, about 4%, about 5%, about 6%, about 7%, about 8%, about 9%, about 10%. In another embodiment, a composition comprises PVP-I at about 0.1% or less, about 0.5% or less, about 1% or less, about 2% or less, about 3% or less, about 4% or less, about 5% or less, about 6% or less, about 7% or less, about 8% or less, about 9% or less or about 10% or less. In another embodiment, a composition comprises PVP-I at about 0.01% or more, about 0.05% or more, about 0.075% or more, about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, about 5% or more, about 6% or more, about 7% or more, about 8% or more, about 9% or more or about 10% or more. In another embodiment, a composition comprises PVP-I at 0.001%, 0.005%, 0.01%, 0.05%, 0.1%, 0.2%, 0.3%, 0.4%, 0.5%, 0.6%, 0.7%, 0.8%, 0.9%, 1.0%, 1.25%, 1.5%, 1.75%, 2.0%, 2.25%, 2.5%, 2.75%, 3.00%, 3.50%, 4.0%, 4.5%, 5.0%, 6.0%, 7.0%, 8.0%, 9.0% or 10.0%.

In an embodiment, a composition comprises DMSO and PVP-I. In an embodiment, a composition consists essentially of DMSO and PVP-I. In an embodiment, a composition consists of DMSO and PVP-I. In an embodiment, a composition is anhydrous. In an embodiment, a composition is substantially anhydrous. In an embodiment, a composition comprises a measurable amount of water.

In an embodiment, anhydrous DMSO is used in a composition. In an embodiment, substantially anhydrous DMSO is used in a composition. It will be understood by one of skill in the art that DMSO can be produced and/or obtained in differing grades, and that one of the variables among DMSO preparations of different grades is the water content. By way of example, DMSO may be completely anhydrous (also referred to herein simply as "anhydrous"), substantially anhydrous, or may contain water to a measurable degree. It will be understood that the amount of measurable water in a DMSO preparation may vary based on limitations of the instrumentation and techniques used to make such measurements. In an embodiment, DMSO that is not completely anhydrous may be substantially anhydrous and contain water at a level below levels of detectability. In an embodiment, DMSO that is not completely anhydrous may contain water, wherein the water content is about at least 0.01%, about at least 0.02%, about at least 0.03%, about at least 0.04%, about at least 0.05%, about at least 0.06%, about at least 0.07%, about at least 0.08%, about at least 0.09%, about at least 0.1%, about at least 0.2%, about at least 0.3%, about at least 0.4%, about at least 0.5%, about at least 0.6%, about at least 0.7%, about at least 0.8%, about at least 0.9%, about at least 1.0%, about at least 1.5%, about at least 2.0%, about at least 2.5%, about at least 5%, about at least 7.5%, about at least 10%, about at least 12.5%, or greater. In an embodiment, DMSO that is not completely anhydrous may contain water, wherein the water content is about less than 0.01%, about less than 0.02%, about less than 0.03%, about less than 0.04%, about less than 0.05%, about less than 0.06%, about less than 0.07%, about less than 0.08%, about less than 0.09%, about less than 0.1%, about less than 0.2%, about less than 0.3%, about less than 0.4%, about less than 0.5%, about less than 0.6%, about less than 0.7%, about less than 0.8%, about less than 0.9%, about less than 1.0%, about less than 1.5%, about less than 2.0%, about less than 2.5%, about less than 5%, about less than 7.5%, about less than 10%, about less than 12.5%, or greater. It will be understood that DMSO may contain one or more other impurities in addition to water.

In an embodiment, a composition comprises at least one of United States Pharmacopeial Convention (USP) grade DMSO, Active Pharmaceutical Ingredient (API) grade DMSO, analytical grade DMSO, and American Chemical Society (ACS) Spectrophotometric grade DMSO. In an embodiment, a composition comprises DMSO having <0.1% water by KF titration and >99.9% determined on an anhydrous basis.

As set forth above, the percent amount of DMSO in a composition is described in a weight-to-weight (w/w) ratio with respect to one or more other components of the composition, unless otherwise indicated. In an embodiment, the weight percent DMSO is the balance of the weight percent after addition of PVP-I. By way of a non-limiting example, a composition may comprise 1 weight percent (1%) PVP-I and 99 weight percent (99%) DMSO. It will be understood that in the foregoing example, the DMSO component of the composition may be completely anhydrous, substantially anhydrous, or may contain water to a measurable degree. In an embodiment, the weight percent DMSO is the balance of the weight percent after addition of PVP-I and any other components (e.g., co-solvent, water, additional active ingredient, etc.). In an embodiment, the weight percent DMSO is the balance of the weight percent after addition of iodophor and other components, if any. In an embodiment, the weight percent penetrant in a composition is the balance of the weight percent after addition of iodophor and other components, if any.

In an embodiment, a composition comprises DMSO in the range of 50% to 99.99%. In an embodiment, a composition comprises DMSO in the range of 1% to 99.99%. In another embodiment, a composition comprises DMSO in the range of 5% and 99.9%. In another embodiment, a composition comprises DMSO in the range of 10% and 99.9%. In another embodiment, a composition comprises DMSO in the range of 20% and 99.9%. In another embodiment, a composition comprises DMSO in the range of 30% and 99.9%. In another embodiment, a composition comprises DMSO in the range of 40% and 99.9%. In another embodiment, a composition comprises DMSO in the range of 50% and 99.9%. In another embodiment, a composition comprises DMSO in the range of 60% and 99.9%. In another embodiment, a composition comprises DMSO in the range of 70% and 99.9%. In another embodiment, a composition comprises DMSO in the range of 80% and 99.9%, and in yet another embodiment, between 90% and 99.9%.

In an embodiment, a composition comprises DMSO in weight percent of about at least 50%, about at least 55%, about at least 60%, about at least 65%, about at least 70%, about at least 75%, about at least 80%, about at least 85%, about at least 87.5%, about at least 90%, about at least 91%, about at least 92%, about at least 93%, about at least 94%, about at least 95%, about at least 96%, about at least 97%, about at least 98%, about at least 99%, or about at least 99.9%. In an embodiment, a composition comprises DMSO at about 1%. In other embodiments, a composition comprises DMSO at about 1%, about 1.5%, about 2%, about 2.5, about 3%, about 3.5%, about 4%, about 4.5%, about 5%, about 5.5%, about 6%, about 6.5%, about 7%, about 7.5%, about 8%, about 8.5%, about 9.0, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 20.5%, about 21%, about 21.5%, about 22%, about 22.5%, about 23%, about 23.5%, about 24%, about 24.5%, about 25%, about 25.5%, about 26%, about 26.5%, about 27%, about 27.5%, about 28%, about 28.5%, about 290%, about 29.5%, about 30%, about 30.5%, about 31%, about 31.50,%, about 32%, about 32.5%, about 33%, about 33.5%, about 34%, about 34.5%, about 35%, about 35.5%, about 36%, about 36.5%, about 37%, about 37.5%, about 38%, about 38.5%, about 39%, about 39.5%, about 40%, about 40.5%, about 41%, about 41.5%, about 42%, about 42.5%, about 43%, about 43.5%, about 44%, about 44.5%, about 45%, about 45.5%, about 46%, about 46.5%, about 47%, about 47.5%, about 48%, about 48.5%, about 49%, about 49.5%, about 50%, about 50.5%, about 510%, about 51.5%, about 52%, about 52.5%, about 53%, about 53.5%, about 54%, about 54.5%, about 55%, about 55.5%, about 56%, about 56.5%, about 57%, about 57.5%, about 58%, about 58.5%, about 59%, about 59.5%, about 60%, about 60.5%, about 61%, about 61.5%, about 62%, about 62.5%, about 636%, about 63.5%, about 64%, about 64.5%, about 65%, about 65.5%, about 66%, about 66.5%, about 67%, about 67.5%, about 68%, about 68.5%, about 69%, about 69.5%, about 70%, about 70.5%, about 71%, about 71.5%, about 72%, about 72.5%, about 73%, about 73.5%, about 74%, about 74.5%, about 75%, about 75.5%, about 76%, about 76.5%, about 77%, about 77.5%, about 78%, about 78.5%, about 79%, about 79.5%, about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, about 99.5%, about 99.9%, or any range determinable from the preceding amounts (for example, about 1% to about 45.5% or about 20.0% to about 49.0%).

In an embodiment, a composition comprises DMSO in weight percent of about 40% to about 50%, about 41% to about 50%, about 42% to about 50%, about 43% to about 50%, about 44, to about 50%, about 45% to about 50%, about 46% to about 50%, about 47% to about 50%, about 48% to about 50%, about 49% to about 50%, 40% to about 49%, about 41% to about 49%, about 42% to about 49%, about 43% to about 49%, about 44% to about 49%, about 45% to about 49, about 46% to about 49%, about 47% to about 49%, about 48% to about 49%, about 40% to about 48%, about 41%6 to about 48%, about 42% to about 48%, about 43% to about 48%, about 44% to about 48%, about 45% to about 48%, about 46% to about 48%, about 47% to about 48%, 40% to about 47%, about 41% to about 47%, about 42% to about 47%, about 43% to about 47%, about 44% to about 47%, about 45% to about 47%, about 46% to about 47%, 40% to about 46%, about 41% to about 46%, about 42% to about 46%, about 43% to about 46%, about 44% to about 46%, about 45% to about 46%, 40%, to about 45%, about 41% to about 45%, about 42% to about 45%, about 43% to about 45%, about 44% to about 45%, 40% to about 44%, about 41% to about 44%, about 42% to about 44%, about 43% to about 44%, 40% to about 43%, about 41% to about 43%, about 42% to about 43%, about 40% to about 42%, about 41% to about 42%, or about 40% to about 41%. In one embodiment, a composition comprises DMSO in weight percent of about 10% to about 30% or about 10% to about 49%. In one embodiment, a composition comprises up to 65% DMSO in weight percent. In one embodiment, a composition comprises up to 60% DMSO in weight percent. In one embodiment, a composition comprises up to 55% DMSO in weight percent. In one embodiment, a composition comprises up to 50% DMSO in weight percent. In one embodiment, a composition comprises up to 49% DMSO in weight percent. In one embodiment, a composition comprises up to 45% DMSO in weight percent. In one embodiment, a composition comprises up to 44% DMSO in weight percent.

In an embodiment, a composition comprises a co-solvent in the range of 1% to 99.99%. In another embodiment, a composition comprises a co-solvent in the range of 5% and 99.9%. In another embodiment, a composition comprises a co-solvent in the range of 10% and 99.9%. In another embodiment, a composition comprises a co-solvent in the range of 20% and 99.9%. In another embodiment, a composition comprises a co-solvent in the range of 30% and 99.9%. In another embodiment, a composition comprises a co-solvent in the range of 40% and 99.9%. In another embodiment, a composition comprises a co-solvent in the range of 50% and 99.9%. In another embodiment, a composition comprises a co-solvent in the range of 60% and 99.9%. In another embodiment, a composition comprises a co-solvent in the range of 70% and 99.9%. In another embodiment, a composition comprises a co-solvent in the range of 80% and 99.9%, and in yet another embodiment, between 90% and 99.9%.

In an embodiment, a composition comprises a co-solvent at about 1%. In other embodiments, a composition comprises a co-solvent at about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99,%.

Examples of co-solvents include, but are not limited to, alcohols, silicones, polyethylene glycol, propylene glycol, glycerin, petrolatum, hydroxymethylcellulose, methylcellulose, and combinations thereof. In an embodiment, a co-solvent is propylene glycol.

In an embodiment, a composition comprises DMSO in the range of about 0.01% to 99.99% and further comprises at least one penetrant in the range of 0.01% to about 99.99%. In an embodiment, a composition comprises DMSO and further comprises at least one penetrant in the range of about 0.1% to about 50%. In another embodiment, a composition comprises DMSO and further comprises at least one penetrant in the range between about 5% and about 50%. In another embodiment, a composition comprises DMSO and further comprises at least one penetrant in the range between about 10% and about 99%. In an embodiment, a composition comprises DMSO, at least one co-solvent, and at least one penetrant. In an embodiment, a co-solvent is also a penetrant.

In an embodiment, where possible, compositions may include pharmaceutically acceptable salts of compounds in the composition. In an embodiment, compositions comprise acid addition salts of the present compounds. In an embodiment, compositions comprise base addition salts of the present compounds. As used herein, the term pharmaceutically acceptable salts or complexes refers to salts or complexes (e.g., solvates, polymorphs) that retain the desired biological activity of the parent compound and exhibit minimal, if any, undesired toxicological effects.

In various embodiments, the compositions encompassed herein comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Protectives and adsorbents include, but are not limited to, dusting powders, zinc sterate, collodion, dimethicone, silicones, zinc carbonate, aloe vera gel and other aloe products, vitamin E oil, allantoin, glycerin, petrolatum, and zinc oxide.

Demulcents include, but are not limited to, benzoin, hydroxypropyl cellulose, hydroxypropyl methylcellulose, and polyvinyl alcohol.

Emollients include, but are not limited to, animal and vegetable fats and oils, myristyl alcohol, alum, and aluminum acetate.

Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol. N-decylmethylsulfoxide, fatty acid esters (e.g., isopropyl myristate, methyl laurate, glycerol monooleate, and propylene glycol monooleate); and N-methylpyrrolidone.

In an embodiment, a composition comprises PVP-I, DMSO, and propylene glycol. In an embodiment, a composition comprises 2% PVP-I, 65% DMSO, 23% and 10% propylene glycol. In an embodiment, the composition is substantially anhydrous.

In an embodiment, a composition comprises PVP-I, DMSO, hydroxymethylcellulose, propylene glycol and glycerin. In an embodiment, a composition comprises 2% PVP-I, about 40% DMSO, and 10-33% propylene glycol and at least one additional inactive ingredient.

In one embodiment, the composition includes 1-3%/o PVP-I, 40-49% DMSO, 8-15% alcohol, 18-25% propylene glycol, 0-2% gelling agents, and 0-3% water. In one embodiment, the composition includes aprotic solvents. In one embodiment, the composition includes 1-3% PVP-I, 10-30% DMSO, 10-35% propylene glycol, 0-2% gelling agents, and 0-3% water. In one embodiment, the composition includes aprotic solvents.

In one embodiment, the invention comprises DMSO 40-50% (w/w), 0.5%-5% PVP-I (w/w) and hydroxypropyl methylcellulose or hydroxymethyl cellulose or hydroxyethyl cellulose.

In one embodiment, the composition is a solution; semi-solid, e.g., a gel, suspension, ointment or cream; tincture; foam; aerosol or another common pharmaceutical dosage form. In one embodiment, the composition is a 2% PVP-I/44% DMSO solution. In one embodiment, the composition is a 1% PVP-I/45% DMSO solution. In one embodiment, the composition is a 1.5% PVP-I/46% DMSO solution. In one embodiment, the composition is a 2.5% PVP-I/43% DMSO solution. In one embodiment, the composition is a 1% PVP-I/99% DMSO solution. In one embodiment, the composition is a 2% PVP-I/65% DMSO solution. In one embodiment, the composition is a 2% PVP-I/65% DMSO/10-25% propylene glycol solution.

Stability

A. Measured as Percent Iodine Remaining

In one embodiment, the formulations are stable at room temperature 25° C. for at least 6 months, 12 months, 18 months and 24 months. Stability is defined as where the final PVP-I concentration is at least 85%-120%, according to the USP method, of the labeled concentration.

In one embodiment, the formulations are stable at room temperature 2-8° C. for at least 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

In one embodiment, the formulations are stable at room temperature −10 to −25° C. for at least 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

In one embodiment, the formulations are stable at room temperature 15-30° C. for at least 6 months, 12 months, 18 months and 24 months. Stability is defined as where the final PVP-I concentration is at least 85%-120%, according to the USP method, of the labeled concentration (e.g. if the label is 2% PVP-I providing for 0.2% iodine, therefore 90% would be 0.18 elemental iodine).

In one embodiment, the formulations are stable at room temperature 40° C. for at least 1 months, 3 months, 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

Methods of Preparation and Use

It is known to one of skill in the art that PVP-I aqueous solutions are difficult to stabilize at low PVP-I concentrations over a long period of time. By way of a non-limiting example, at concentrations of PVP-I less than about 0.7% (w/w, aqueous), PVP-I aqueous solutions rapidly decay to yield complex mixtures of iodinated and iodine-free constituents.

As described herein, it was surprisingly found that in the aprotic DMSO solvent system encompassed by the disclosure set forth herein, PVP-I solutions as low as 0.1% can be easily prepared and maintained as stable compositions in Type I glass or HDPE plastic for long periods of time. Also as described herein, hydrated DMSO solutions prepared from aqueous PVP-I demonstrate increased stability for the PVP-I component.

In an embodiment, a composition comprises dry, solid or powdered PVP-I dissolved or suspended in a composition comprising or consisting of DMSO. In another embodiment, DMSO is added to an aqueous preparation comprising or consisting of PVP-I. Based on the disclosure herein, one of skill in the art will understand how to prepare a composition to arrive at the desired amounts of iodine, iodophor, and DMSO, among other possible components of the compositions encompassed herein.

By way of a non-limiting example, a therapeutically-effective pharmaceutical composition is prepared using solid PVP-I, which is dissolved or suspended in DMSO. In an aspect, the composition is anhydrous. In an aspect, the composition is substantially anhydrous. In another embodiment, DMSO can be added to aqueous solutions of PVP-I to prepare a therapeutically-effective pharmaceutical composition. In an embodiment, DMSO is used in the range of 500%-99% as a co-solvent with water and other non-aqueous co-colvents. In an embodiment, a formulation includes one or more excipients. By way of a non-limiting example, excipients include, but are not limited to, sodium chloride, sodium dihydrogen phosphate monohydrate, disodium hydrogen phosphate anhydrous and water, as well as others known to those skilled in the art.

In an embodiment, a composition is prepared by adding 10% PVP-I (w/v, aqueous) to pure DMSO q.s. to yield a resulting solution of 1% PVP-I (w/w) with DMSO. In another embodiment, compositions are prepared by dissolving solid PVP-I in pure DMSO q.s to obtain any of 0.1%, 0.2%, 0.3%, 0.4%, 0.5%, 1.0%, 1.25%, 1.5%, 2.0%, or 2.5% PVP-I (w/w), as well as about 0.1%, about 0.2%, about 0.3%, about 0.4%, about 0.5%, about 1.0%, about 1.25%, about 1.5%, about 2.0%, or about 2.5% PVP-I (w/w) compositions, with DMSO as the solvent. In yet another embodiment, compositions are prepared by dissolving solid PVP-I in pure DMSO q.s to obtain any composition set forth, described, and/or encompassed herein. Similar compositions comprising aqueous PVP-I (with and without excipients commonly used and/or known in the art) and DMSO can be prepared from a stock 10% PVP-I aqueous solution and pure DMSO. It will be understood by the skilled artisan, however, that any starting composition of PVP-I, solid or liquid, may be used when the appropriate dilutions and adjustments are made to result in the desired final PVP-I concentration. Similarly, any starting composition of iodophor or elemental iodine may be used when the appropriate dilutions and adjustments are made to result in the desired final iodophor or elemental iodine concentration, respectively.

It will be understood, based on the disclosure set forth herein, in view of the skill in the art, that specific dosage for compounds and compositions encompassed herein may be determined empirically through clinical and/or pharmacokinetic experimentation, and that such dosages may be adjusted according to pre-specified effectiveness and/or toxicity criteria. It will also be understood that a specific dosage and treatment regimen for any particular patient will depend upon a variety of factors, including the activity of the specific compounds employed, the characteristics of the patient, drug combination, the judgment of the treating physician and the nature and severity of the particular disease or condition being treated.

In an embodiment, a therapeutic composition is prepared by optimizing one or more compounds for use in a dosage form different than that which is typically used for the compound. In an embodiment, a compound that is not typically administered in a topical dosage form is developed for use in a topical dosage form. The chemical and biological assays required for such development are known to one of skill in the art. The disclosure herein provides the skilled artisan with the guidance as to how to prepare such compounds and compositions comprising such compounds.

In an embodiment, a method of treating a subject having an ocular surface disease complicated by microbial colonization and/or infection includes administration of a composition set forth, described, and/or encompassed herein to treat the ocular surface disease, and the treatment of the ocular surface disease includes at least one of preventing or slowing the progression of the infection, preventing the spread of the infection, eradicating at least some of the infection, and eradicating the entire infection.

In an embodiment, a therapeutic composition is administered on a schedule once a day. In an embodiment, a therapeutic composition is administered twice a day. In an embodiment, a therapeutic composition is administered three times a day, four times a day, five times a day, or more. In an embodiment, a therapeutic composition is administered less frequently than once a day. In an embodiment, a therapeutic composition is administered once every two days, once every three days, once every four days, once every five days, once every six days, or once every seven days. In an embodiment, a therapeutic composition is administered less frequently than once a week. In an embodiment, a therapeutic composition is administered once a month. In an embodiment, a therapeutic composition is administered twice a month.

In an embodiment, a therapeutic dosing regimen is continued for at least one day, at least two days, at least three days, at least four days, at least five days, at least six days, or at least seven days. In an embodiment, a therapeutic dosing regimen is continued for at least one week, at least two weeks, at least three weeks, at least four weeks, at least six weeks, at least eight weeks, at least ten weeks, at least twelve weeks, at least fourteen weeks, or at least sixteen weeks. In an embodiment, a therapeutic dosing regimen is continued for at least one month, at least two months, at least three months, at least four months, at least five months, at least six months, at least nine months, or at least twelve months.

The invention is further described by the following examples. In an aspect, the following examples demonstrate effective and/or successful treatment of the identified conditions using compositions and methods encompassed by the present disclosure. It should be recognized that variations based on the inventive features are within the skill of the ordinary artisan, and that the scope of the invention should not be limited by the examples. To properly determine the scope of the invention, an interested party should consider the claims herein, and any equivalent thereof. The entire disclosure of international patent applications, PCT/US2012/036942 and PCT/US2012/065298 are hereby incorporated herein by reference as if fully set forth herein. In addition, all citations herein are incorporated by reference, and unless otherwise expressly stated, all percentages are by weight/weight.

Additional examples of useful compositions described in this invention include the formulation of creams, petrolatum balms, salves, sprays, and other formulations well known to those in the art suitable for topical administration to the ocular surface or are "ophthalmically acceptable" compositions.

While the foregoing written description enables a person ordinarily skilled in the art to reproduce and use what is considered presently to be the best mode thereof, those of ordinary skill will understand and appreciate the existence of variations, combinations, derivatives, analogs and equivalents of the specific embodiments, methods and examples provided above. The invention should therefore not be limited by the above described embodiments, examples and methods by instead by all embodiments, examples and methods within the scope and spirit of the present invention.

Clinical Trial Results and Clinical Efficacy

In a 12-week clinical trial for treatment of HPV verrucous warts, substantial improvement, defined by a +2 or greater change in investigator-graded Global Aesthetic Improvement Score, is shown by reaching the endpoint of complete eradication and/or substantial reduction in the total number of warts and/or reduction in the size of wart or lesion. This result is achieved in about 20%, about 30%, about 40%, about 50%, about 60%, about 70%, about 80% or about 90% of study subjects. Clinical success, defined as achieving the primary endpoint in at least 20% of study subjects, is achieved with QD, BID, TID or QID dosing.

Subjects are dosed twice per day for a period of 12 weeks. Subjects are male or female, between the ages of 10-99, presenting with visible verrucous warts. Liquid formulations are generally be expected to be more efficacious than gel formulations because the lower viscosity, compared to that of gels, is expected to allow the active ingredient to be more easily transferred across the epidermal layer or the generally less penetrable, horny outer layer of the wart. Dosing of the gel formulation comprises administration of an approximately ½ inch ribbon directly to the wart (2×/day for 12 weeks) and/or the area immediately surrounding the wart. Dosing of the liquid formulation comprises administration of 1-5 drops, typically 2-3 drops, of the composition directly to the wart and/or area immediately surrounding the wart.

The below chart summarizes the exemplary and unexpected results, showing a gel formulation of the invention as more effective against warts than a liquid formulation of the subject invention.

| LIQUID FORMULATION [PVPI 2%, DMSO44%, Glycerin 44%, propylene glycol 10%] | Active Arm (N = 11) | Vehicle (N = 6) |
|---|---|---|
| Resolution of warts | 6/11 = 55% | 2/6 = 33% |
| No change in warts | 4/11 = 36% | 2/6 = 33% |
| Warts Worse | 1/11 = 9% | 2/6 = 33% |

| GEL FORMULATION [PVPI 2%, DMSO44%, 4% Hydroxyethylcellulose, 50% water] | Active Arm (N = 18) | Vehicle (N = 8) |
|---|---|---|
| Resolution of warts | 13/18 = 72.2%% | 2/8 = 25% |
| No change in warts | 4/18 = 22.2% | 3/8 = 37.5% |
| Warts Worse | 1/18 = 5.6% | 3/8 = 37.5% |

The efficacy of wart treatment using a gel formulation of the invention (2% PVP-I; 44% DMSO; 4% hydroxyethyl cellulose; 50% water) in 39 clinical subjects is summarized in Table 1, below:

TABLE 1

Summary of Wart Patients Treated With PVPI/DMSO

| # | Age/Gender | V1 | V2 | V3 | V4 | % Resolved | Location | Formulation | Adverse Events |
|---|---|---|---|---|---|---|---|---|---|
| 1 | 6/F | 3 | 2 | 0 | N/S | 100 | Ante-cub fossa | 2% solution | None |
| 2 | 6/F | 12 | 8 | 3 | 3 | 75 | b/l knees | 2% solution | Atopic Flare at Site |
| 3 | 12/F | 6 | 2 | 0 | N/S | 66 | Right elbow | 2% solution | None |
| 4 | 10/M | 23 | 12 | 4 | 3 | 87 | Left axilla/shoulder | 2% solution | None |
| 5 | 3/F | 3 | 0 | N/S | N/S | 100 | chin | 2% solution | None |
| 6 | 3/M | 6 | 4 | 4 | N/S | 33 | Left forearm | 2% solution | None |
| 7 | 5/M | 8 | 2 | 0 | N/S | 100 | Peri-oral | 2% solution | none |
| 8 | 17/F | 15 | 10 | 3 | 3 | 80 | Inner thighs | 2% solution | None |
| 9 | 13/F | 10 | 0 | 0 | N/S | 100 | elbows | 2% solution | None |
| 10 | 10/M | 10 | 4 | 4 | N/S | 60 | Left neck | 2% solution | Lesion Inflamed |
| 11 | 7/M | 2 | 1 | 0 | 0 | 100 | Right axilla | 2% solution | None |
| 12 | 5/M | 1 | 0 | N/S | N/S | 100 | Left cheek | 2% gel | None |
| 13 | 4/F | 1 | 0 | 0 | N/S | 100 | Right rib cage | 2% gel | None |
| 14 | 9/F | 4 | 1 | 1 | 0 | 100 | Right abdomen | 2% gel | None |
| 15 | 3/M | 15 | 6 | 2 | 2 | 87 | Neck | 2% gel | None |
| 16 | 5/M | 9 | 2 | 1 | 0 | 100 | Neck | 2% gel | None |
| 17 | 6/F | 12 | 10 | 2 | N/S | 83 | Left forearm | 2% gel | None |
| 18 | 9/F | 10 | 3 | 0 | N/S | 100 | Right axilla | 2% gel | None |
| 19 | 4/F | 1 | 0 | N/S | N/S | 100 | Right cheek | 2% gel | None |
| 20 | 10/M | 8 | 0 | 0 | N/S | 100 | Penis | 2% gel | Mild Irritation |
| 21 | 8/M | 4 | 1 | 1 | 0 | 100 | Left thigh | 2% gel | None |
| 22 | 12/F | 2 | 0 | N/S | N/S | 100 | Right bicep | 2% gel | None |
| 23 | 17/F | 100+ | 20 | 2 | 0 | 100 | Inner thighs | 2% gel | None |
| 24 | 4/M | 15 | 14 | 4 | 3 | 80 | Left rib cage | 2% gel | None |
| 25 | 5/M | 7 | 5 | 0 | N/S | 100 | Abdomen/back | 2% gel | None |
| 26 | 6/F | 2 | 0 | N/S | N/S | 100 | Upper lip | 2% gel | None |
| 27 | 10/F | 4 | 1 | 0 | N/S | 100 | buttocks | 2% gel | None |
| 28 | 3/F | 10 | 5 | 3 | N/S | 70 | Abdomen/ribs | 2% gel | Mild Irritation |
| 29 | 5/F | 5 | 0 | N/S | N/S | 100 | Left cheek | 2% gel | Mild Irritation |
| 30 | 8/M | 3 | 0 | N/S | N/S | 100 | Right upper medial arm | 2% gel | None |
| 31 | 11/M | 8 | 2 | 1 | 0 | 100 | Left knee/shin | 2% gel | None |
| 32 | 9/F | 6 | 4 | 2 | N/S | 66 | Right ante-cubital | 2% gel | None |
| 33 | 9/F | 3 | 5 | 4 | 2 | 33 | Left ribs | 2% gel | Atopic Flare |
| 34 | 4/M | 4 | 0 | 0 | N/S | 100 | Cutaneous lip | 2% gel | None |
| 35 | 5/M | 7 | 3 | N/S | N/S | 57 | Buttocks/penis | 2% gel | None |
| 36 | 4/F | 8 | 1 | 0 | 0 | 100 | labia | 2% gel | Mild Irritation |
| 37 | 3/F | 2 | 0 | N/S | N/S | 100 | Left thigh | 2% gel | None |
| 38 | 6/F | 2 | 0 | N/S | N/S | 100 | Neck | 2% gel | None |
| 39 | 4/F | 35 | 10 | 4 | 3 | 91 | Buttocks/thighs | 2% gel | None |

For molluscum contagiousm, the PVP-I 2% gel formulation has been found to be more efficacious than the PVP-I 2% solution. The solution takes 1-2 minutes to fully absorb, and as molluscum primarily occurs in the pediatric population this waiting period is often not adhered to and some of the solution is inadvertently wiped off. The gel has much better contact time and does not require a waiting period once applied to the skin. For the solution, a complete clearance was seen in 5/11 (45%) patients and partial clearance in 6/11 (55%) patients, with 79/98 (81%) total lesions resolving. For the gel, a complete response was seen in 20/28 (71%) patients and partial response seen in 8/28 (29%) patients, with 268/288 (93%) of total lesions clearing.

In a 12-week clinical trial for treating blepharitis, the endpoint of complete eradication and/or the endpoint of substantial reduction in the signs and symptoms of blepharitis. The results from a randomized, controlled clinical trial demonstrates the effectiveness a formulation of the subject invention comprising 2% povidone-iodine, with a penetration enhancer, DMSO, which can successfully eliminate blepharitis. The blepharitis infections are assessed at 2-week intervals, with complete resolution demonstrated by the 12-week clinical assessment. By the end of a 12-week study complete resolution of signs and symptoms of blepharitis in at least 10%, at least 15%, at least 20%, at least 30% or at least 40% of study subjects is observed by the 12-week end-of-study visit.

In addition, a recent study of 18 patients showed that a gel formulation comprising 0.25% or 0.5% PVP-I exhibits less irritation when administered to the Lower Lid Conjunctival Fornix. These results are summarized in Table 2, below:

TABLE 2

Ocular Irritation Study Using 0.25% PVP-I/DMSO
(Dose "A") Gel or 0.5% PVP-I/DMSO (Dose "B")
Gel In OD Lower Lid Conjunctival Fornix[1]

| Patient Number | Dose Applied | Discharge | Injection (redness) | Burning | Itch |
|---|---|---|---|---|---|
| 001 | A | 0 | 0 | 0 | 0 |
| 002 | A | 0 | 0 | 0 | 0 |
| 003 | A | 0 | 0 | 0 | 0 |
| 004 | A | 0 | 0 | 0 | 0 |
| 005 | A | 1 | 0 | 0 | 0 |
| 006 | A | 1 | 0 | 0 | 0 |
| 007 | A | 0 | 0 | 0 | 0 |
| 008 | A | 1 | 0 | 0 | 0 |
| 009 | A | 0 | 0 | 0 | 0 |
| 010 | A | 0 | 0 | 0 | 0 |
| 011 | A | 0 | 1 | 1 | 0 |
| 012 | A | 0 | 0 | 1 | 0 |
| 013 | B | 0 | 0 | 0 | 0 |
| 014 | B | 0 | 0 | 0 | 0 |
| 015 | B | 1 | 0 | 0 | 0 |
| 016 | B | 1 | 0 | 1 | 0 |
| 017 | B | 1 | 1 | 1 | 0 |
| 018 | B | 0 | 1 | 1 | 0 |

[1]All applications are ½" ribbon applied directly into lower lid conjunctival fornix; all grading for all signs and symptoms is 0-3 on a 4 point scale where 0 = absent, 1 = mild, 2 = moderate and 3 = severe.

In the examples from the clinical trials above, a liquid formulation was expected to provide adequate efficacy against warts and blepharitis. Most wart treatments are liquids. Surprisingly, it was found that a gel formulation provides unexpected advantages and increased efficacy compared with similar concentrations of PVP-I in a liquid formulation.

EXAMPLES

Example 1

Anterior Blepharitis; Treated with 1.0% PVP-I in 30% USP Grade DMSO with Polypropylene Glyclol and Hydroxymethylcellulose This patient was suffering from anterior blepharitis. In this common type of blepharitis, the anterior lid margin demonstrates madarosis, collarettes, scurf, lash debris and bacterial overgrowth. The lid margin may also be erythematous along with the conjunctiva and a decreased tear break up time is present. In this patient the condition had persisted for over 7 years and taken a chronic course. The patient had tried numerous antibiotics, steroids, lid scrubs, omega 3 fatty acids, and anti-inflammatories without benefit. Prepared was a composition as disclosed herein using 1.0% PVP-I in 30% DMSO with polypropylene glycol and hydroxymethylcellulose. The patient was treated by applying the solution topically to the eyelid and conjunctiva twice daily. Within one week improvement was noted in and around the eyelid. After two weeks the condition rapidly improved, as the conjunctival erythema abated, tear break up time and dry eye symptoms normalized. Close inspection of the anterior lid eyelid margin revealed healthy cilia without associated debris or bacterial overgrowth.

Example 2

Posterior Blepharitis; Treated with 0.2% PVP-I in 35%% USP Grade DMSO with Hydroxyethyl Cellulose This patient was suffering from posterior blepharitis. In this most common type of blepharitis, the posterior lid margin demonstrates meibomian gland thickening, keratinization, fat saponification, and dilated, telangectatic lid vessels. The lid margin may also be erythematous along with the conjunctiva and decreased tear break up time is evident. In this patient the condition had persisted for over 7 years and taken a chronic course. The patient had tried numerous antibiotics, steroids, lid scrubs, omega 3 fatty acids and anti-inflammatories without benefit. Prepared was a composition as disclosed herein using 0.2% PVP-I in 35%% DMSO with hydroxyethyl cellulose. The patient was treated by applying the solution topically to the eyelid and conjunctiva twice daily. Within one week improvement was noted in and around the eyelid. After two weeks the condition rapidly improved, as the conjunctival erythema abated, tear break up time and dry eye symptoms normalized. Close inspection of the posterior lid eyelid margin revealed healthy meibomian seecretions, attenuation of posterior lid blood vessels and lack of erythema.

Example 3

A. Rosacea Blepharitis; Treated with 0.5% PVP-I in 38% USP Grade DMSO with Hydroxyethyl Cellulose This patient was suffering from Rosacea blepharitis. In this type of blepharitis, the posterior lid margin demonstrates meibomian gland thickening, keratinization, fat saponification, and dilated, telangectatic lid vessels. Anterior lid margin may also demonstrate scurf and bacterial overgrowth. The lid margin may also be erythematous along with the conjunctiva and a decreased tear break up time is present. In this patient the condition had persisted for over 7 years and taken a chronic course. The patient had tried numerous antibiotics, steroids, lid scrubs, omega 3 fatty acids and anti-inflammatories without benefit.

Prepared was a composition as disclosed herein using 0.5% PVP-I in 38% DMSO with hydroxyethyl cellulose. The patient was treated by applying the solution topically to the eyelid and conjunctiva twice daily. Within one week improvement was noted in and around the eyelid. After two weeks the condition rapidly improved, as the conjunctival erythema abated, tear break up time and dry eye symptoms normalized. The dilated, tortuous posterior lid margin vessels had significantly attenuated and meibomian secretions were healthy. Close inspection of the anterior lid eyelid margin revealed healthy cilia without associated debris or bacterial overgrowth.

B. Rosacea Blepahritis; Treated with 1% PVP-I in 44% USP Grade DMSO with 4% Hydroxyethylcellulose in Water A 78 year old male with a past ocular history of glaucoma and pseudophakia presented with long standing ocular dryness, grittiness, periocular erythema and eyelid crusting. On facial inspection, nasal and facial telangiectasia with flushing were evident. His topical medical regimen included Latanoprost 1 drop QHS OU, Brimonidine 1 drop BID OU, and Dorzolamide, Timolol 1 drop BID OU. The patient endorsed utilization of a variety of medicines and treatments to abate this condition, however, they were of little benefit. Failed therapies included topical steroids, antibiotics including azithromycin, combination medicines, and cyclosporine. Oral medicines including doxycycline and DHA/ALA/EPA were also ineffective.

Slit lamp biomicroscopic examination revealed bilateral anterior lid margin erythema, crusting and thickening. Lash examination revealed some breakage with scurf-like deposition. Inspection of the posterior eyelids revealed inspissated meibomian glands with capping and turbid secretions. Further towards the posterior tarsal area, dilated, engorged telangiectatic vessels were present. The marginal lid erythema extended not only to the tarsal plate, but also to the inferior bulbar conjunctiva. Tear break-up time was notably decreased and corneae revealed inferior, bilateral punctate epithelial erosions. A diagnosis of rosacea blepharoconjunctivitis was made.

The patient was given a topical gel of 1% PVP-I in a dimethylsulfoxide (DMSO) vehicle that was prepared from a licensed compounding pharmacy. The treatment was administered twice daily and delivered by rubbing the gel onto the lash line and eyelid. At the first follow up visit one week later, remarkable improvements were noted. Most prominently, much of the conjunctivitis, anterior lid erythema and thickening had reversed. The patient was instructed to decrease the gel to once daily, but continue treatment for a total of one month. At this second follow up visit, not only were the initial improvements conserved, but the posterior lid margin vessels and telangiectasia had begun to attenuate and involute. Moreover, meibomian capping was no longer present and secretions were less viscous. Besides occasional mild tingling at the application site, the patient reported no other adverse effects Example 4

Demodex Blepharitis; Treated with 1.0% PVP-I in 40% USP Grade DMSO with Petrolatum This patient was suffering from anterior Demodex blepharitis. In this type of blepharitis, the anterior lid margin demonstrates madarosis, collarettes in cylindrical pattern and lash debris. Decreased tear break up time is also evident. The posterior lid margin may also be erythematous and demonstrate meibomian inspissation, fat saponification, and bacterial overgrowth. In this patient the condition had persisted for over 7 years and taken a chronic course. The patient had tried numerous antibiotics, steroids, tea tree oils, lid scrubs omega 3 fatty acids and anti-inflammatories without benefit. Cilia were epilated and examined under the microscope positively identifying Demodex folliculorum. Prepared was a composition as disclosed herein using 1.0% PVP-I in 40% DMSO with petrolatum. The patient was treated by applying the solution topically to the eyelid and conjunctiva twice daily. Within one week improvement was noted in and around the eyelid. After two weeks the condition rapidly improved, as the conjunctival erythema abated, tear break up time and dry eye symptoms were normalized. Posterior lid margin demonstrated normal meibomian secretions. Microscopic assessment of cilia was negative for Demodex mites.

Example 5

Blepharoconjunctivitis, Treated with 0.3% PVP-I in 33% USP Grade DMSO with Glycerin This patient was suffering from blepharoconjunctivits. In this type of ocular inflammation, the anterior lid margin demonstrates madarosis, collarettes, scurf, lash debris and bacterial overgrowth. The posterior lid margin may also be erythematous, and demonstrate meibomian inspissation, capping, and keratinization. A hallmark of this process is abundant conjunctival injection which is secondary to anterior and posterior lid inflammation. In this patient the condition had persisted for over 1 week with an acute course. The patient had tried numerous antibiotics, steroids, lid scrubs, omega 3 fatty acids, and anti-inflammatories without benefit. Prepared was a composition as disclosed herein using 0.3% PVP-I in 33% DMSO with glycerin. The patient was treated by applying the solution topically to the eyelid and conjunctiva twice daily. Within one week improvement was noted in and around the eyelid. After two weeks the condition rapidly improved, as tear break up time and dry eye symptoms normalized. Close inspection of the anterior lid eyelid margin revealed healthy cilia without associated debris or bacterial overgrowth. Posterior lid margin inspection revealed healthy meibomian secretions and decreased lid erythema. The conjunctival examination revealed quiet and healthy tissue without inflammation.

Example 6

Adenoviral Conjunctivitis; Treated with 0.15% PVP-I in 44% USP Grade DMSO with Polyvinylpyrrolidone This patient was suffering from adenoviral conjunctivitis. This common type of conjunctivitis follows a recent viral upper respiratory infection or contact with another infected person. Pre-auricular adenopathy is often present. In this patient, the conjunctiva demonstrated diffuse injection with chemosis. There was frequent clear ocular discharge present. Eyelid eversion revealed 3+ follicular reaction with few scattered petechiae. RPS Adenodetector sampling identified the causative agent to be an Adenovirus serotype. The patient had tried numerous antibiotics, steroids, lid scrubs and anti-inflammatories without benefit. Prepared was a composition as disclosed herein using 0.15% PVP-I in 48% DMSO with polyvinylpyrrolidone. The patient was treated by applying the solution topically to the eyelid and conjunctiva three times daily. Within one week improvement was noted in and around the eyelid evidenced by decreased chemosis and lid edema. At two weeks the condition was resolved, as the conjunctival erythema, discharge and follicles were no longer present. There was no development of corneal infiltrates or pseudomembranes.

Example 7

Epidemic Adenoviral Conjunctivitis: Treated with 0.5% PVP-I in 41.5%% USP Grade DMSO with Hydroxyethyl Cellulose This patient was suffering from epidemic adenoviral conjunctivitis. This type of conjunctivitis follows a recent viral upper respiratory infection or contact with another infected person. Pre-auricular adenopathy is often present. In this patient, the conjunctiva demonstrated diffuse injection with chemosis along with pseudomembrane formation. There was frequent clear ocular discharge present. Eyelid eversion revealed 3+ follicular reaction with few scattered petechiae. Corneal examination showed multifocal, sub-epithelial infiltrates. RPS Adenodetector sampling identified the causative agent to be an Adenovirus serotype. The patient had tried numerous antibiotics, steroids, lid scrubs and anti-inflammatories without benefit. Prepared was a composition as disclosed herein using 0.5% PVP-I in 41.5% DMSO with hydroxyethyl cellulose. The patient was treated by applying the solution topically to the eyelid and conjunctiva three times daily. Within one week improvement was noted in and around the eyelid. At two weeks the condition was resolved, as the conjunctival erythema, discharge, follicles and pseudomembranes were no longer present. The corneal infiltrates had also resolved and the cornea was clear and compact.

Example 8

Bacterial Conjunctivitis; Treated with 0.7% PVP-I in 31.5% USP Grade DMSO with Polypropylene Glycol This patient was suffering from bacterial conjunctivitis. In this type of conjunctivitis there is often bacterial overgrowth and infiltration of the conjunctival epithelial layers. In this patient, conjunctiva also demonstrated diffuse injection with chemosis along with inflammatory membrane formation. There was frequent purulent ocular discharge present. Eyelid eversion revealed 3+ inflamed palpebral conjunctiva with few petechiae. Conjuctival cultures identified the causative agent as *Staphylococcus Aureus*. The patient had tried numerous antibiotics, steroids, lid scrubs and anti-inflammatories without benefit. Prepared was a composition as disclosed herein using 0.7% PVP-I in 31.5% DMSO with polypropylene glycol. The patient was treated by applying the solution topically to the eyelid and conjunctiva three times daily. Within three days improvement was noted in and around the eyelid. At one week the condition was resolved, as the conjunctival erythema, discharge, follicles and inflammatory membranes were no longer present.

Example 9

Herpes Simplex Virus Epithelial Keratitis; Treated with 2.0% PVP-I in 49% USP Grade DMSO with Glycerin This patient was suffering from herpes simplex virus epithelial keratitis. In this type of keratitis there is often active replicating virus present within epithelial dendrites. With immune system weakening, the virus reactivates in the sensory ganglia and descends to infect the cornea. It can often manifest as recurrent disease. In this patient, the conjunctiva demonstrated diffuse injection and the cornea showed staining epithelial ulcerations in serpentine or dentritic form with terminal bulbs. Millipore testing reveals herpes simplex virus as the causative agent. The patient had tried numerous antibiotics, steroids, oral and topical anti-virals and anti-inflammatories without benefit. Prepared was a composition as disclosed herein using 2.0% PVP-I in 49% DMSO with glycerin. The patient was treated by applying the solution topically to the eye three times daily. Within three days improvement was noted in and around the eye. The dendrites began to re-epithelialize and active virus replication was halted. At one week the condition was resolved and there was no evidence of the previous corneal lesions. The conjunctiva was white and quiet.

Example 10

Herpes Simplex Virus Stromal Keratitis; Treated with 0.15% PVP-I in 44% USP Grade DMSO with Hydroxyethyl Cellulose This patient was suffering from herpes simplex virus stromal keratitis. In this type of keratitis there is often immune activation of the host secondary to molecular mimicry causing stromal corneal swelling. There may or may not be active replicating virus. It can often manifest as recurrent disease. In this patient, the conjunctiva demonstrated diffuse injection and the cornea showed diffuse corneal swelling with opacification. The patient had tried numerous antibiotics, steroids, oral and topical anti-virals and anti-inflammatories without benefit. Prepared was a composition as disclosed herein using 0.15% PVP-I in 44% DMSO with hydroxyethyl cellulose. The patient was treated by applying the solution topically to the eye three times daily. Within three days improvement was noted in and around the eye. The stromal edema began to clear and the patient was without any staining dendrites. At one week the condition was resolved and there was no evidence of the previous corneal lesions, cicatrization, or neovascularization. The conjunctiva was white and quiet.

Example 11

Herpes Simplex Virus Endothelial Keratitis; Treated with 1.4% PVP-I in 38% USP Grade DMSO with Hydroxyethyl Cellulose This patient was suffering from herpes simplex virus endothelial keratitis. In this type of keratitis there is often immune activation of the host secondary to molecular mimicry directed at endothelial cells. There may or may not be active replicating virus. It can often manifest as recurrent disease. In this patient, the conjunctiva demonstrated diffuse injection and the cornea showed disciform endothelial inflammation with keratic precipitates. Some stromal corneal edema was also present. The anterior chamber revealed rare inflammatory cells and mild trabeculitis. The patient had tried numerous antibiotics, steroids, oral and topical anti-virals and anti-inflammatories without benefit. Prepared was a composition as disclosed herein using 1.4% PVP-I in 38% DMSO with hydroxyethyl cellulose. The patient was treated by applying the solution topically to the eye three times daily. Within three days improvement was noted in and around the eye. The stromal edema began to clear and the keratic precipitates attenuated. The anterior chamber cell and flare was no longer present. At one week the condition was resolved and there was no evidence of the previous corneal swelling. There was no residual corneal cicatrization, or neovascularization. The conjunctiva was white and quiet.

Example 12

Herpes Zoster Ophthalmicus; Treated with 1.8% PVP-I in 40% USP Grade DMSO with Petralatum This patient was suffering from herpes zoster virus epithelial keratitis. In this type of keratitis there is often viral infection within the eye along with erythematous macules and excoriations in dermatomal distribution. With immune system weakening, the herpes zoster virus is reactivated within the ophthalmic division of the trigeminal nerve. In this patient, the conjunctiva demonstrated diffuse injection and the cornea showed rose bengal staining epithelial "stuck on" dendrites in without terminal bulbs. The underlying corneal stroma demonstrated central edema without keratic precipitates. Fundus examination was negative for vasculitis. The patient had tried numerous antibiotics, steroids, oral and topical anti-virals and anti-inflammatories without benefit. Prepared was a composition as disclosed herein using 1.8% PVP-I in 40% DMSO with petralatum. The patient was treated by applying the solution topically to the eye three times daily. Within three days improvement was noted in and around the eye. The dendrites began to re-epithelialize and active virus replication was halted. At one week the condition was resolved and there was no evidence of the previous corneal lesions. The conjunctiva was white and quiet and the cornea was clear and compact.

Example 13

Gram Positive Bacterial Corneal Ulceration; Treated with 0.35% PVP-I in 45% USP Grade DMSO with Petralatum This patient was suffering from a bacterial corneal ulceration. In this type of infection there is often a history of contact lens use, however, this is not a prerequisite. Bacteria is introduced into the eye through a small break in the epithelium and gains foothold to the underlying structures. In this patient, the conjunctiva demonstrated diffuse injection with pyogenic discharge. The cornea demonstrated a central, three millimeter circular infiltrate with overlying central epithelial defect. The infiltrate induced stromalysis and the resultant cornea had thinned by approximately thirty percent. There was a one millimeter layered hypopyon in the anterior chamber. Corneal cultures were taken, and Coagulase negative Streptococcal species were identified. The patient had tried numerous antibiotics, steroids, oral and topical anti-virals and anti-inflammatories without benefit. Prepared was a composition as disclosed herein using 0.35% PVP-I in 45% DMSO with petralatum. The patient was treated by applying the solution topically to the eye six times daily. Within three days improvement was noted in and around the eye. The corneal melt had halted and re-epithelialization had taken place. At one week the hypopyon had resolved, the conjunctiva cleared and a small central infiltrate remained. By week two, the patient was healed and no active bacterial infection remained. A central corneal cicatrix was evident in the area of previous active infiltrate.

Example 14

Gram Negative Bacterial Corneal Ulceration; Treated with 0.2% PVP-I in 36% USP Grade DMSO with Polyvinylpyrrolidone This patient was suffering from a bacterial corneal ulceration. In this type of infection there is often a history of contact lens use, however, this is not a prerequisite. Bacteria is introduced into the eye through a small break in the epithelium and gains foothold to the underlying structures. In this patient, the conjunctiva demonstrated diffuse injection with pyogenic discharge. The cornea demonstrated a central, five millimeter circular infiltrate with overlying central epithelial defect. The infiltrate had induced abundant stromalysis and the resultant cornea had thinned by approximately seventy five percent. There was a two millimeter layered hypopyon in the anterior chamber. Corneal cultures were taken, and *Pseudomonas aeruginosa* species was identified. The patient had tried numerous antibiotics, steroids, oral and topical anti-virals and anti-inflammatories without benefit. Prepared was a composition as disclosed herein using 0.2% PVP-I in 36% DMSO with polyvinylpyrrolidone. The patient was treated by applying the solution topically to the eye six times daily. Within three days improvement was noted in and around the eye. The corneal melt had halted and re-epithelialization had taken place. At one week the hypopyon had resolved, the conjunctiva cleared and a small central infiltrate remained. By week two, the patient was healed and no active bacterial infection remained. A central corneal cicatrix was evident in the area of previous active infiltrate.

Example 15

Fungal Corneal Ulceration; Treated with 1.2% PVP-I in 45% USP Grade DMSO with Glycerin This patient was suffering from a fungal corneal ulceration. In this type of infection there is often a history of contact lens use, however, this is not a prerequisite. Fungus is introduced into the eye through a small break in the epithelium and gains foothold to the underlying structures. In this patient, the conjunctiva demonstrated diffuse injection with pyogenic discharge. The cornea contained multifocal, feather-like infiltrates with overlying central epithelial defect. The infiltrates had induced minimal stromalysis and the resultant cornea was not thinned. There was no hypopyon, however, cell and flare were present. Corneal cultures were taken, and *Fusarium* species was identified. The patient had tried numerous antifungals, antibiotics, steroids, oral and topical anti-virals and anti-inflammatories without benefit. Prepared was a composition as disclosed herein using 1.2% PVP-I in 45% DMSO with glycerin. The patient was treated by applying the solution topically to the eye six times daily. Within one week improvement was noted in and around the eye. The cornea had begun the process of re-epithelialization. At two weeks corneal infiltrate was resolved, the conjunctiva had cleared and the anterior chamber was quiet. A central corneal cicatrix was evident in the area of previous active infiltrate.

Example 16

*Acanthamoeba* Corneal Ulceration; Treated with 0.4% PVP-I in 39% USP Grade DMSO with Hydroxyethyl Cellulose This patient was suffering from an *Acanthamoeba* corneal ulceration. In this type of infection there is often a history of contact lens use and home-made contact lens solutions, however, this is not a prerequisite. *Acanthamoeba* parasites are often introduced into the eye through a small break in the epithelium and gains foothold to the underlying structures. The patient endorses pain out of proportion with examination. In this patient, the conjunctiva demonstrated diffuse injection. The cornea contained multiple bullous lesions with enlarged corneal nerves. There was an overlying epithelial defect and faint ring-shaped infiltrate. The infiltrate had induced minimal stromalysis and the resultant cornea was not thinned. There was no hypopyon, however, cell and flare were present. Corneal cultures were taken, and *Acanthamoeba* species were identified on non-nutrient agar with *E. coli* overlay. The patient had tried numerous anti-amoeboid medicines including chlorhexidine, propamidine, antifungals, antibiotics, steroids, oral and topical anti-virals and anti-inflammatories without benefit. Prepared was a composition as disclosed herein using 0.4% PVP-I in 39% DMSO with hydroxyethyl cellulose. The patient was treated by applying the solution topically to the eye six times daily. Within one week improvement was noted in and around the eye. The corneal had begun the process of re-epithelialization and the ring ulcer began to lessen in intensity. At two weeks the corneal infiltrate was resolved, the conjunctiva cleared and perineuralgia abated. A central corneal cicatrix was evident in the area of previous active infiltrate.

Example 17

Conjunctival Intraepithelial Neoplasia; Treated with 1.1% PVP-I in 47% USP Grade DMSO Polypropylene Glycol This patient was suffering from conjunctival intraepithelial neoplasia. In this type of dysplasia cells grow irregularly within the epithelium but do not break through the basement membrane. It is often associated with UV exposure, smoking, or human papilloma virus. In this patient, the conjunctiva demonstrated growth a fleshy limbal mass with leukoplakia. A prominent feeder vessel was present. The irregular area stained positively with rose bengal. Conjunctival biopsy was taken and pathology report confirmed the diagnosis. The patient had tried numerous topical chemotherapeutic agents such as mitomycin and interferon. Eventual excision with cryotherapy was performed, however, the lesion recurred. Prepared was a composition as disclosed herein using 1.1% PVP-I in 47% DMSO with polypropylene glycol. The patient was treated by applying the solution topically to the eye four times daily. Within one month improvement was noted in the eye. The conjunctival lesion had begun to involute and lessen in surface area. At two months there had been complete regression of the lesion with healthy appearing conjunctiva. Post-treatment biopsy in the affected area was negative.

Example 18

Conjunctival Squamous Cell Carcinoma; Treated with 1.5% PVP-I in 32%% USP Grade DMSO with Polyvinylpyrrolidone This patient was suffering from a conjunctival squamous cell carcinoma. In this type of dysplasia cells grow irregularly within the epithelium and break through the basement membrane into the conjunctival stroma. It is often associated with UV exposure, smoking, or human papilloma virus. In this patient, the conjunctiva demonstrated a fleshy limbal mass with leukoplakia. A prominent feeder vessel was present. The irregular area stained positively with rose bengal. Conjunctival biopsy was taken and pathology report confirmed the diagnosis. The patient had tried numerous topical chemotherapeutic agents such as mitomycin and interferon. Eventual excision with cryotherapy was performed, however, the lesion recurred. Prepared was a composition as disclosed herein using 1.5% PVP-I in 32% DMSO with polyvinylpyrrolidone. The patient was treated by applying the solution topically to the eye four times daily. Within one month improvement was noted in the eye. The conjunctival lesion had begun to involute and lessen in surface area. At two months there had been complete regression of the lesion with healthy appearing conjunctiva. Post-treatment biopsy in the affected area was negative.

Example 19

Corneal Intraepithelial Neoplasia; Treated with 0.6% PVP-I in 33% USP Grade DMSO with Polyvinylpyrrolidone This patient was suffering from a corneal intraepithelial neoplasia. In this type of dysplasia cells grow irregularly within the corneal epithelium but do not break through the basement membrane. It is often associated with UV exposure, smoking, or human papilloma virus. In this patient, the cornea demonstrated a diffuse translucent gray growth with leukoplakia. The irregular area stained positively with rose bengal. Corneal biopsy was taken and pathology report confirmed the diagnosis. The patient had tried numerous topical chemotherapeutic agents such as mitomycin and interferon. Eventual excision with cryotherapy was performed, however, the lesion recurred. Prepared was a composition as disclosed herein using 0.6% PVP-I in 33% DMSO with polyvinylpyrrolidone. The patient was treated by applying the solution topically to the eye four times daily. Within one month improvement was noted in the eye. The corneal lesion had begun to involute and diminish in surface area. At two months there had been complete regression of the lesion with healthy appearing cornea. Post-treatment biopsy in the affected area was negative.

Example 20

Corneal Squamous Cell Carcinoma; Treated with 0.1% PVP-I in 30.5% USP Grade DMSO with Hydroxyethyl Cellulose This patient was suffering from a corneal squamous cell carcinoma. In this type of dysplasia cells grow irregularly within the corneal epithelium and break through the basement membrane to invade deeper structures. It is often associated with UV exposure, smoking, or human papilloma virus. In this patient, the cornea demonstrated a diffuse translucent gray growth with leukoplakia. The irregular area stained positively with rose bengal. Corneal biopsy was taken and pathology report confirmed the diagnosis. The patient had tried numerous topical chemotherapeutic agents such as mitomycin and interferon. Eventual excision with cryotherapy was performed, however, the lesion recurred. Prepared was a composition as disclosed herein using 0.1% PVP-I in 30.5% DMSO with hydroxyethyl cellulose. The patient was treated by applying the solution topically to the eye four times daily. Within one month improvement was noted in the eye. The corneal lesion had begun to involute and diminish in surface area. At two months there had been complete regression of the lesion with healthy appearing cornea. Post-treatment biopsy in the affected area was negative.

Example 21

Conjunctival Squamous Papilloma; Treated with 1.9% PVP-I in 46% USP Grade DMSO with Petralatum This patient was suffering from a conjunctival papilloma. In this type of dysplasia conjunctival cells demonstrate an exophytic or cauliflower-like pattern. They may also grow in a finger-like pattern and are often lobulated with vascular cores. The process is often associated with UV exposure, smoking, or human papilloma virus. In this patient, the conjunctiva demonstrated an exophytic mass with a pedunculated base, frond-like growth and vascular core. Conjunctival biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 1.9% PVP-I in 46% DMSO with petralatum. The patient was treated by applying the solution topically to the eye four times daily. Within one month improvement was noted in the eye. The conjunctival lesion had begun to involute and diminish surface area. At two months there had been complete regression of the lesion with healthy appearing underlying conjunctiva. Post-treatment biopsy in the affected area was negative.

Example 22

Corneal Squamous Papilloma; Treated with 0.8% PVP-I in 43% USP Grade DMSO with Polyvinylpyrrolidone This patient was suffering from a corneal squamous papilloma. In this type of dysplasia corneal cells demonstrate an exophytic or cauliflower-like pattern. They may also grow in a finger-like pattern and are often lobulated with vascular cores. The process is often associated with UV exposure, smoking, or human papilloma virus. In this patient, the cornea demonstrated an exophytic mass with a pedunculated base, frond-like growth and vascular core. Corneal biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 0.8% PVP-I in 43% DMSO with polyvinylpyrrolidone. The patient was treated by applying the solution topically to the eye four times daily. Within one month improvement was noted in the eye. The corneal lesion had begun to involute and diminish in surface area. At two months there had been complete regression of the lesion with healthy appearing corneal tissue. Post-treatment biopsy in the affected area was negative.

Example 23

Eyelid Squamous Papilloma; Treated with 1.7% PVP-I in 47% USP Grade DMSO with Hydroxyethyl Cellulose This patient was suffering from an eyelid squamous papilloma. In this type of dysplasia, cells demonstrate an exophytic or cauliflower-like pattern. They may also grow in a finger-like pattern and are often lobulated with vascular cores. The process is often associated with UV exposure, smoking, or human papilloma virus. In this patient, the eyelid lamellae demonstrated an exophytic mass with a pedunculated base, frond-like growth and vascular core. Eyelid biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 1.7% PVP-I in 47% DMSO with hydroxyethyl cellulose. The patient was treated by applying the solution topically to the eye four times daily. Within one month improvement was noted. The eyelid lesion had begun to involute and diminish in surface area. At two months there had been complete regression of the lesion with healthy appearing eyelid tissues and structures.

Example 24

Eyelid Verrucae; Treated with 0.1% PVP-I in 43% USP Grade DMSO with Polypropylene Glycol This patient was suffering from an eyelid verrucae. This type of eyelid growth usually commences with gray or tan papules that progress to hyperkeratotic lesions with a papillomatous surface. The process is often associated with human papilloma virus infection of the epithelial layers. In this patient, the superior eyelid demonstrated a solid white growth with a papillomatous surface. Eyelid biopsy was taken and pathology report confirmed the diagnosis. The patient had tried numerous topical agents without benefit. Cryotherapy was eventually performed, however, the lesion recurred. Prepared was a composition as disclosed herein using 0.1% PVP-I in 43% DMSO with polypropylene glycol. The patient was treated by applying the solution topically to the eyelid structures four times daily. Within two weeks improvement was noted. The lesion had begun to involute and diminish in surface area. At one month there had been complete regression of the lesion with healthy appearing eyelid tissues and skin.

Example 25

Eyelid Molluscum Contagiosum; Treated with 0.9% PVP-I in 39% USP Grade DMSO with Hydroxyethyl Cellulose This patient was suffering from an eyelid associated molluscum contagiosum. This type of eyelid infection usually demonstrates flesh colored, dome-shaped pearly papules with a dimpled centers. The process is often associated with pox virus infection of the epithelial layers. In this patient, the upper eyelid and lid margin demonstrated multiple flesh colored papules with dimpled centers. The patient had tried numerous topical agents without benefit including salicylic acid and imiquimod. Cryotherapy with excision was eventually performed, however, the lesions recurred. Prepared was a composition as disclosed herein using 0.9% PVP-I in 39% DMSO with hydroxyethyl cellulose. The patient was treated by applying the solution topically to the eyelid and margin structures four times daily. Within two weeks improvement was noted. The lesions had begun to involute and diminish in surface area. At one month there had been complete regression of the lesions with healthy appearing eyelid tissues and lamellae.

Example 26

Eyelid Antisepsis Prior to Cataract Surgery, Treated with 0.2% PVP-I in 44% USP Grade DMSO Hydroxyethyl Cellulose This patient was suffering from an anterior and posterior blepharitis prior to cataract surgery. Numerous ophthalmic studies have implicated bacteria that populate the eyelids and conjunctiva as those being responsible for post-operative infectious endophthalmitis. It is therefore routine to attempt to sterilize these surfaces prior to commencing said procedure. In this patient, the posterior lid margin demonstrated meibomian gland thickening, keratinization, fat saponification, and dilated, telangectatic lid vessels. The anterior lid margin also demonstrated scurf and bacterial overgrowth. The patient had tried numerous topical agents to sterilize the ocular surface including topical antibiotics and antiseptics without benefit. Prepared was a composition as disclosed herein using 0.2% PVP-I in 44% DMSO with hydroxyethyl cellulose. The patient was treated by applying the solution topically to the eye and eyelid three times daily commencing 3 days prior to the procedure. On the day of the procedure, conjunctival cultures were taken and demonstrated no growth. The patient underwent a successful procedure and had an uneventful post-operative course.

Example 27

Eyelid Antisepsis Prior to Intravitreal Injection; Treated with 1.4% PVP-I in 32% USP Grade DMSO with Glycerin This patient was suffering from an anterior and posterior blepharitis prior to intravitreal injection. Numerous ophthalmic studies have implicated bacteria that populate the eyelids and conjunctiva as those being responsible for post-injection infectious endophthalmitis. It is therefore routine to attempt to sterilize these surfaces prior to commencing said procedure. In this patient, the posterior lid margin demonstrated meibomian gland thickening, keratinization, fat saponification, and dilated, telangectatic lid vessels. The anterior lid margin also demonstrated scurf and bacterial overgrowth. The patient had tried numerous topical agents to sterilize the ocular surface including topical antibiotics and antiseptics without benefit. Prepared was a composition as disclosed herein using 1.4% PVP-I in 32% DMSO with glycerin. The patient was treated by applying the solution topically to the eye and eyelid three times daily commencing 3 days prior to the procedure. On the day of the procedure, conjunctival cultures were taken and demonstrated no growth. The patient underwent a successful injection and had an uneventful post-operative course.

The invention claimed is:

1. A topical gel composition comprising
   0.1% to 10% povidone-iodine (PVP-I);
   30% to 99% dimethyl sulfoxide (DMSO); and
   1% to 10% gelling agent;
   wherein said topical gel composition exhibits greater efficacy or stability for treating skin or eye infection, compared to a liquid composition substantially free of a gelling agent and comprising 0.1% to 10% povidone-iodine and 30% to 99% DMSO.

2. The composition of claim 1, comprising 0.5% to 5% PVP-I.

3. The composition of claim 1, comprising 40% to 49% DMSO.

4. The composition of claim 1, comprising 1% to 4% gelling agent.

5. The composition of claim 1, comprising:
   0.1%-5% PVP-I;
   44% DMSO;
   1% to 3% hydroxyethylcellulose; and
   aqueous solvent.

6. The composition of claim 1, wherein the gelling agent is selected from the group consisting of a gum, agar, petrolatum, and a cellulosic polymer.

7. The composition of claim 1, wherein the gelling agent is hydroxyethyl cellulose.

8. A method of treating an infection of the skin, eye, or eyelid, said method comprising the step of:
   applying to a site of the infection as needed to reduce or eliminate the infection, an effective amount of a topical gel composition comprising
   0.1% to 10% povidone-iodine (PVP-I);
   30% to 99% dimethyl sulfoxide (DMSO); and
   1% to 10% gelling agent;
   wherein said topical gel composition exhibits greater efficacy or stability for treating skin or eye infection, compared to a liquid composition substantially free of a gelling agent and comprising 0.1% to 10% povidone-iodine and 30% to 99% DMSO.

9. The method of claim 8 wherein said infection is caused by or associated with one or more infectious agents selected from the group consisting of bacteria, demodex, fungus or yeast, and virus.

10. The method of claim 9 wherein the virus infectious agent is human papilloma virus (HPV).

11. The method of claim 8 wherein the infection is an infectious condition of the skin of the face or genitalia.

12. The method of claim 9, wherein the infectious condition is caused by or associated with an infectious agent which is a virus.

13. The method of claim 9, wherein the infectious condition is caused by or associated with an infectious agent which is *demodex*.

* * * * *